United States Patent
Chaudhuri

(10) Patent No.: US 6,602,515 B2
(45) Date of Patent: Aug. 5, 2003

(54) PHOTO STABLE ORGANIC SUNSCREEN COMPOUNDS WITH ANTIOXIDANT PROPERTIES AND COMPOSITIONS OBTAINED THEREFROM

(75) Inventor: Ratan K. Chaudhuri, Lincoln Park, NJ (US)

(73) Assignee: EM Industries, Hawthorne, NY (US)

( * ) Notice: Subject to any disclaimer, the term of this patent is extended or adjusted under 35 U.S.C. 154(b) by 102 days.

(21) Appl. No.: 09/904,904

(22) Filed: Jul. 16, 2001

(65) Prior Publication Data

US 2003/0108492 A1 Jun. 12, 2003

(51) Int. Cl.[7] .............. A61K 6/00; A61K 7/42; C07C 69/74; C07C 69/76; C07C 61/00; C07C 205/00

(52) U.S. Cl. .............. 424/401; 424/59; 560/1; 560/55; 562/400; 568/306

(58) Field of Search ............ 424/401, 59; 560/55, 560/1; 562/400; 568/306

(56) References Cited

U.S. PATENT DOCUMENTS

| | | |
|---|---|---|
| 3,256,312 A | 6/1966 | Strobel |
| 3,272,855 A | 9/1966 | Strobel |
| 3,275,520 A | 9/1966 | Strobel |
| 3,278,448 A | 10/1966 | Lauerer |
| 3,470,233 A | 9/1969 | Hans-Joachin Bohn et al. |
| 3,535,424 A | 10/1970 | Fujimoto |
| 3,860,598 A | 1/1975 | Rosenkranz |
| 3,928,324 A | 12/1975 | Rosati |
| 3,928,429 A | 12/1975 | El-Chahawi |
| 4,335,054 A | 6/1982 | Blaser |
| 4,457,911 A | 7/1984 | Conner |
| 4,504,419 A | 3/1985 | Dexter |
| 4,515,774 A | 5/1985 | Conner |
| 4,592,906 A | 6/1986 | Baker |
| 4,613,499 A | 9/1986 | Conner |
| 4,647,589 A | 3/1987 | Valone |
| 4,726,942 A | 2/1988 | Lang |
| 4,797,493 A | 1/1989 | Matsuno |
| 4,971,996 A | 11/1990 | Shiraishi |
| 4,985,237 A | 1/1991 | Matsuno |
| 5,057,538 A | 10/1991 | Shiraishi |
| 5,063,243 A | 11/1991 | Cho |
| 5,124,354 A | 6/1992 | Green |
| 5,175,340 A | 12/1992 | Forestier et al. |
| 5,177,259 A * | 1/1993 | Connor et al. ............ 560/35 |
| 5,185,370 A | 2/1993 | Backstrom |
| 5,218,000 A | 6/1993 | Usherwood |
| 5,283,352 A | 2/1994 | Backstrom |
| 5,326,785 A | 7/1994 | Cho |
| 5,451,694 A | 9/1995 | Kuhn |
| 5,478,856 A * | 12/1995 | Suzuki et al. ............ 514/340 |
| 5,514,711 A | 5/1996 | Kitano |
| 5,516,839 A | 5/1996 | Ishidoya |
| 5,538,716 A | 7/1996 | Forestier |
| 5,601,811 A | 2/1997 | Gallagher |
| 5,654,465 A | 8/1997 | Qian |
| 5,670,140 A | 9/1997 | DeFlandre |
| 5,738,842 A | 4/1998 | Raspanti |
| 5,817,862 A | 10/1998 | Poetsch |
| 5,830,441 A | 11/1998 | Wang |
| 5,888,481 A | 3/1999 | Horn |
| 5,951,968 A | 9/1999 | Forestier |
| 6,066,327 A * | 5/2000 | Gubernick et al. ......... 424/401 |
| 6,090,374 A | 7/2000 | Habeck |

FOREIGN PATENT DOCUMENTS

| | | |
|---|---|---|
| DE | 2816819 | 10/1979 |
| EP | 0631177 | 12/1994 |
| JP | 64-13017 * | 1/1989 |

OTHER PUBLICATIONS

Wright et al, "Organic NLO Polymers," Macromolecules, 1994, 27, 3009–3015; published Dec. 1994.*
XP–002218456 Abstract of JP 01 013017 A(Pola Kasei Kogyo KK), Jan. 1989.
XP–002218455 – Knoevenagel, E. et al., Chem. Ber., vol. 37, 1904, pp. 4476–4482.
XP–002048362 – Gazit A. et al. "Tyrphostins I: Synthesis And Biological Activity Of Protein Tyrosine Kinase Inhibitors" Journal of Medicinal Chemistry, American Chemical Society, Washington, U.S., vol. 32, No. 19, 1989, pp. 2344–2352.
XP–002193484 – Sohda T. et al., "Antiulcer activity of 5–benzylthiazolidine–2,4–dione derivatives" Chemical And Pharmaceutical Bulletin, Pharmaceutical Society of Japan, Tokyo, JP, vol. 31, No. 2, Feb. 1983 pp. 560–569.
XP001109032 Cho, H. et al., J. Med. Chem., vol. 34, 1991, pp. 1503–1506.

* cited by examiner

*Primary Examiner*—Sreeni Padmanabhan
*Assistant Examiner*—Michael A. Willis
(74) *Attorney, Agent, or Firm*—Millen, White, Zelano & Branigan, P.C.

(57) ABSTRACT

A compound of formula I

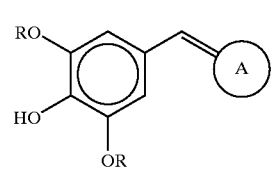

wherein

A is a moiety which provides UV absorbing activity to the compound of formula I that comprises 1 divalent group or 2 monovalent groups, with at least one group having carbonyl (C=O) functionality, and each R is independently linear or branched $C_1$–$C_8$ alkyl. Sunscreen formulations which contain these compounds and methods using these compounds to prepare formulations are also provided.

34 Claims, 7 Drawing Sheets

PHOTO STABLE ORGANIC SUNSCREEN COMPOUNDS WITH ANTIOXIDANT PROPERTIES AND COMPOSITIONS OBTAINED THEREFROM

BACKGROUND OF THE INVENTION

Topical sunscreen compositions are commonly used during outdoor work or leisure as a means for providing protection of exposed skin against acute and chronic adverse effects of solar radiation such as sunburn, cancer and photoaging. Many effective sunscreen preparations are sold commercially or are described in cosmetic or pharmaceutical literature. In general sunscreen preparations are formulated as creams, lotions or oils containing as the active agent an ultra violet radiation absorbing chemical compound. The sunscreen functions by blocking passage of ultra violet radiation thereby preventing its penetration into the skin.

According to Zecchino et al. (U.S. Pat. No. 5,008,100), sunscreen agents may be characterized in the order of decreasing effectiveness as either highly chromophoric (monomeric organic compounds and inorganic compounds such as titanium dioxide) and minimally chromophoric (polymeric organic solids).

Organic sunscreens are classified into UV-A filters, UV-B filters or broad spectrum filters (UV-A and UV-B functionality in a single molecule) depending on the type of radiation they absorb. UV-A sunscreens absorb radiation in the 320 to 400 mn regions of the ultra violet spectrum and UV-B sunscreens absorb radiation in the 290 to 320 nm regions of the ultra violet spectrum.

Broad band sunscreens (UV-A and UV-B functionality) absorb radiation in the 290 to 400 nm region of the ultra violet spectrum and have two maximums, one in the UV-B region and the other in the UV-A region.

Representative references related to UV sunscreens are:

U.S. Pat. No. 3,278,448, which discloses cinnamic acid derivatives such as 4-hydroxy, 3-5-ditertbutyl-alphacarbethoxy-cinnamic acid ether ester in column 2, line 20;

U.S. Pat. No. 3,538,226, which describes cinnamic acid alkyl ester derivatives at column 1, lines 15–31 and column 2, lines 1–12 and column 3, lines 30–55 and 60;

U.S. Pat. No. 5,175,340, which describes cinnamic acid alkyl esters having hydroxy radicals and alkoxy radicals on the phenyl ring, and U.S. Pat. No. 5,830,441, which describes UV absorbents containing a cyano or cinnamyl moiety by the generic formula at col. 2, lines 1–21.

Other references which disclose cinnamide compounds include U.S. Pat. Nos. 5,601,811, 4,335,054, 5,124,354, 5,294,643 and 5,514,711.

Unfortunately, some of the highly chromophoric monomeric organic compounds employed in sunscreen compositions are not photostable and the protection from sun damage is lost. For example, Avobenzone, a UV-A sunscreen, is highly photo-unstable. In addition to lack of photostability of many organic sunscreens, they do not possess an antioxidant property which is essential for protecting skin or hair.

The ideal sunscreen formulation should be nontoxic and non-irritating to the skin tissue and be capable of convenient application in a uniform continuous film. The product should be chemically and physically stable so as to provide an acceptable shelf life upon storage. It is particularly desirable that the preparation should retain its protective effect over a prolonged period after application. Thus, the active agent when present on the skin must be resistant to chemical and/or photo degradation.

Techniques for stabilizing UV absorbent compositions are known. Representative disclosures in this area include U.S. Pat. Nos. 5,567,418, 5,538,716, 5,951,968 and 5,670,140.

Antioxidants are believed to function by providing protection from free-radical damage. To be an effective quencher, it is believed the antioxidant must be present in an adequate concentration at the site of free radical generation. Since antioxidants are used in low concentrations and are a separate ingredient, they may not be available at the site of generation, thereby reducing the desired skin protection. Based on these drawbacks, it is desirable to provide the antioxidant and photostable sunscreen functionality in a single molecule to enhance the effectiveness of the antioxidant properties.

SUMMARY OF THE INVENTION

There is provided by the present invention compounds with sunscreen activity, i.e. they are chromophoric within the ultra violet radiation range of from 290–400 nm and they also exhibit antioxidant properties. These compounds are represented by general formula I

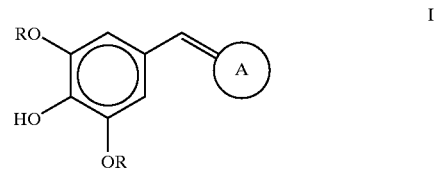

I

In formula I, A is a moiety which provides chromophoric properties within the UV radiation range of 290–400 nm. This moiety comprises one divalent group or two monovalent groups with at least one group having carbonyl (C=O) functionality. For formula I, each R is independently linear or branched $C_1$–$C_8$ alkyl. The one or more compounds of formula I can preferably stabilize an additional sunscreening agent against photodegradation from exposure to sunlight. Preferred compounds are of formula II below.

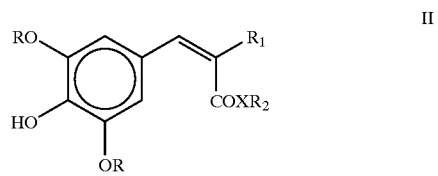

II

For formula II, each R is independently linear or branched $C_1$ to $C_8$ alkyl;

$R_1$ is selected from the group consisting —C(O)CH$_3$, —CO$_2$R$_3$, —C(O)NH$_2$, —C(O)N(R$_4$)$_2$, and —CN;

X is O or NH;

$R_2$ is linear or branched $C_1$ to $C_{20}$ alkyl;

$R_3$ is linear or branched $C_1$ to $C_{20}$ alkyl; and each $R_4$ is independently hydrogen or linear or branched $C_1$ to $C_8$ alkyl.

Included within the preferred compounds are those of formula II wherein R is linear or branched $C_1$–$C_4$ alkyl, X is oxygen and $R_2$ is linear or branched $C_1$–$C_{12}$ alkyl. Of these compounds, those more preferred have $R_1$ as C(O)CH$_3$ or CO$_2$R$_3$ wherein $R_3$ is a linear or branched $C_1$ to $C_4$ alkyl. For compounds wherein $R_1$ is C(O)N(R$_4$)$_2$, $R_4$ is preferably hydrogen or a linear or branched $C_1$–$C_4$ alkyl.

While compounds having from $C_1$–$C_4$ alkyl groups for $R_2$ and $R_3$ are preferred, significant utility can be obtained from compounds wherein $R_2$ and $R_3$ are linear or branched $C_8$ to $C_{20}$ alkyl or $C_{12}$ to $C_{20}$ alkyl groups.

Another preferred class of compounds are those of formulae III and IV wherein $R_1$ and $R_2$ are as defined for formula I with $R_3$ being $C_1$–$C_8$ alkyl and $R_4$ being $C_1$–$C_4$ alkyl.

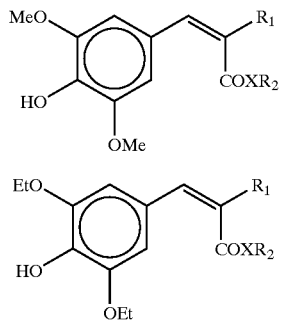

Preferred compounds include those selected from the group consisting of ethyl- alpha- cyano-3,5-dimethoxy-4-hydroxy cinnamate, ethyl- alpha- acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4- hydroxy benzylidene malonate, didodecyl-3,5-dimethoxy-4-hydroxy benzylidene malonate, dipalmitoyl-3,5-dimethoxy-4-hydroxy benzylidene malonate, and di-isopropyl-3,5-dimethoxy-4-hydroxy benzylidene malonate.

The present invention also provides sunscreen formulations which comprise a compound of formula I, II, III and/or IV. These sunscreen formulations are effective in absorbing illumination in the range of wavelengths of 320 nm and above. Amounts of the compounds of formula I, II, III and/or within such compositions typically range from 0.1 to 40 wt % based on the total weight of the sunscreen. These sunscreen formulations can contain one or more additional organic sunscreen agents for filtering UV-B or UV-A rays or they may additionally contain one or more metal oxide sunscreen agents such as titanium dioxide or zinc oxide.

These sunscreen formulations may additionally contain a carrier and at least one component selected from the group consisting of dispersing agents, preservatives, anti-foams, perfumes, oils, waxes, propellants, dyes, pigment emulsifiers, surfactants, thickeners, humectants, exfoliants and emollients. These sunscreen formulations may be in the form of a cosmetic composition with a cosmetically acceptable carrier and one or more cosmetic adjuvants. The sunscreen formulation can optionally have conventional antioxidants or other stabilizers which do not have UV absorbing characteristics.

Methods of using these sunscreen compositions and methods for improving the photostability of sunscreen formulations are also provided. The methods of using the sunscreen formulations comprise applying a sunscreen formulation which contains a compound of formula I, II, III and/or IV to a substrate. Preferred substrates are skin and hair. To improve the photostability of a sunscreen formulation, a compound of formula I, II, III and/or IV is added to the sunscreen formulation in an amount sufficient to reduce the loss of UV absorbance of the sunscreen as it is irradiated. Typical amounts fall within the range of 0.1% to 40 wt %, based on the total weight of said sunscreen formulation. More typically, the amount falls within the range of 1 wt % to 25 wt %. The amount of organic sunscreen compound of formulae I, II, III and/or IV, preferably ranges from about 3 wt % to about 15 wt % of the sunscreen formulation. Other ingredients referred to above and discussed more particularly below are generally used in an amount from about 0.1 wt % to about 10 wt % of the sunscreen formulation. The balance comprises a cosmetically or pharmaceutically acceptable carrier.

The sunscreen formulations of this invention preferably offer protection from UV radiation with wavelengths of about 290 nm to 400 nm and preferably from wavelengths in the range of about 290–370 nm. Sunscreen formulations of this invention also typically have a sunscreening protection factor (SPF) range of from about 2 to 60, with a preferred SPF range of from about 10 to about 45. The target SPF range can be achieved with a combination of both inorganic and organic chromophoric compounds. SPF is determined by techniques well known in the art, on human skin as described in the Federal Register, Aug. 25, 1978, Vol. 43, No. 166, pages 38259–38269 (□Sunscreen Drug Products for Over-The-Counter Human Use□, Food and Drug Administration). SPF values can also be approximated using in-vitro models as described, for example, in J. Soc. Cosmet. Chem. 44:127–133 (May/June 1989).

The sunscreen formulations may contain dispersing agents, emulsifiers or thickening agents to assist in applying a uniform layer of the active compounds. Suitable dispersing agents for the sunscreen formulations include those useful for dispersing organic or inorganic sunscreen agents in either a water phase, oil phase, or part of an emulsion, including, for example, chitosan.

Emulsifiers may be used in the sunscreen formulations to disperse one or more of the compounds of formulae I, II, III and/or IV or other component of the sunscreen formulation. Suitable emulsifiers include conventional agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the sunscreen formulations. Suitable thickening agents include carbomers, acrylate/acrylonitrile copolymers, xanthan gum and combinations of these. The carbomer thickeners include the crosslinked CARBOPOLO□ acrylic polymers from B.F. Goodrich. The amount of thickener within the sunscreen formulation, on a solids basis without water, may range from about 0.001 to about 5%, preferably from 0.01 to about 1% and optimally from about 0.1 to about 0.5% by weight.

Minor optional adjunct ingredients for the sunscreen formulations to be applied to skin or hair may include preservatives, waterproofing agents, fragrances, anti-foam agents, plant extracts (Aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethyolpropane siloxysilicate, chitosan, dimethicone, polyethylene, polyvinylpyrrolidone (PVP), polyvinylpyrrolidone/vinylacetate, PVP/Eiconsene copolymer and adipic acids/diethylene glycol/glycerine crosspolymer etc. Waterproofing agents may be present at levels of from about 0.01 to about 10% by weight.

The sunscreen formulations may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably alkylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the sunscreen composition.

The exfoliants suitable for use in the present may be selected from alpha-hydroxy carboxylic acids, beta hydroxycarboxylic acids and salts of these acids. Most preferred are glycolic, lactic and salicylic acids and their alkali, metal or ammonium salts.

Suitable emollients include those agents known for softening the skin or hair which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric glycerides, propylene glycol dicaprylate/dicaprate and decyl oleate.

The sunscreen formulations may optionally contain one or more inorganic sunscreen agents as discussed above including micro fine surface treated titanium dioxide and micro fine untreated and surface treated zinc oxide. Titanium dioxide in the sunscreen compositions preferably has a mean primary particle size of between 5 and 150 nm and preferably from 10 to 100 nm. Titanium oxide may have anatase, ratile or amorphous structure. The zinc oxide in the sunscreen compositions preferably has a mean primary particle size of between 5 nm and 150 nm, preferably between 10 nm and 100 nm. Examples of modified titanium dioxide compositions include:

Eusolex® T-45D (surface treated with alumina and simethicone, 45% dispersion in isononoyl isononoate);

Eusolex® T-Aqua, (surface treated with aluminum hydroxide, 25% dispersion in water); and Eusolex® T-2000 (surface treated with alumina and simethicone), all available from MERCK KGaA.

The sunscreen formulation may also contain one or more additional monomeric organic chromophoric compounds. These can either be UV-A, UV-B or broad band filters. Examples of suitable UV-A sunscreens include benzophenone derivatives, menthyl anthranilate, butyl methoxydibenzoyl methane and benzylidene-dioxoimidazoline derivatives. Examples of suitable UV-B sunscreens include cinnamate derivatives, salicylate derivatives, para-aminobenzoic acid derivatives, camphor derivatives, phenylbenzimidazole derivatives and diphenylacrylate derivatives. Examples of suitable broad-band sunscreen include benzotriazole derivatives and triazine derivatives such as anisotriazone. Others include ethylhexyltriazone and diethylhexylbutamidotriazone.

Particularly useful organic sunscreen agents that can be introduced are Avobenzone, 2-ethylhexyl p-methoxycinnamate, 4,4'-t-butylmethoxydibenzoyl methane, 2 hydroxy-4-methoxybenzophenone, octyldimethyl p-aminobenzoic acid, 2,2-dihydroxy-4-methoxybenzophenone, ethyl-4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-5-sulfonic acid, 2-(p-dimethylamino phenyl-5-sulfoniobenzoxazoic acid and mixtures thereof.

Examples of useful commercially available organic sunscreen agents that can be introduced include 2-phenylbenzimidazole-5-sulphonic acid, 2-(4-methylbenzylidene)-camphor, 4-isopropyldibenzoyl methane all of the Eusolex™ series sold by EM Industries and Merck KGaA, Darmstadt, Germany.

Although not preferred, the sunscreen formulation may contain an additional antioxidant. Examples of suitable antioxidants which provide stability include p-hydroxybenzoic acid and its derivatives (ethylisobutyl, glyceryl esters of p-hydroxybenzoic acid); salicylates (octylamyl, phenyl, benzyl menthyl, glycerol and dipropyleneglycol esters); cumarin derivatives; flavones; hydroxy or methoxy substituted benzophenones; uric or tannic acid and its derivatives; hydroquinone; and benzophenones.

In addition to providing sunscreen activity at levels which provide U.V. absorbtion, the compounds of Formula 1 can be introduced into a skin care formulation, a hair care formulation or other personal care formulations such as cosmetic formulations at levels which provide antioxidant activity. These compounds can be used with or without conventional antioxidants in personal care formulations such as hair care, skin care and cosmetic formulations.

The personal care formulations can be in the form of creams, ointments, suspensions, powders, oil, lotions, oleo alcoholic lotions, fatty gels, oleo-alcoholic gels and lotions, solid sticks, foams, emulsions, liquid dispersions, sprays and aerosols. More specific forms include: lipsticks, foundations, makeup, loose or press powder, eye blush, eye shadow and nail lacquer.

Sunscreen formulations of this invention can be prepared as described in Formulations 1–7 by conventional means.

FORMULATION 1

| Phase A | | Phase B | |
|---|---|---|---|
| Deionized water | 60.0% | Ethyl-alpha-acetyl-3,5-dimethoxy-4-hydroxy cinnamate | 8.75% |
| Disodium EDTA | .10% | Octyl salicylate | 5% |
| Glycerin | 1.5% | Aluminum stearate | 5% |
| NaCl | 3.0% | Cyclomethicone/dimethicone | 10% |
| Butylene glycol | 2.5% | Cetyl dimethicone | 1% |
| | | Cyclomethicone | 2% |
| | | ABIC-EM 97 | 1% |
| | | Fragrance | .15% |

Procedure:

Combine phase B ingredients. Stir and heat to 70–75° C. Combine Phase A ingredients. Heat while stirring to 70–75° C. Add Phase B to Phase A while stirring. Add preservative. Stir, allowing mixture to cool to room temperature.

| Formulation 2: Sunscreen Oil/Water Spray Lotion | | |
|---|---|---|
| INCI Name | Trade Name (Supplier) | % w/w |
| Phase A-1 | | |
| Di-isopropyl-3,5-dimethoxy-4-hydroxybenzylidene malonate-(Example VIII) | | 7.50 |
| Benzophenone-3 | Eusolex ® 4360 (Rona) | 2.50 |
| Dicapryl ether | Cetiol ® OE (Henkel) | 4.50 |
| Dimethicone | Dow Corning 200 ®, 50 cst (Dow) | 2.00 |
| Stearyl Alcohol | Crodacol S-70 (Croda) | 0.60 |
| PPG-2 Ceteareth-9 | Eumulgin ® L (Henkel) | 0.40 |
| Steareth-10 | Volpo 10 (Croda) | 0.50 |
| Glyceryl stearate, PBG-100 Stearate | Arlacel ® 165 (ICI) | 2.80 |
| Phase A-2 | | |
| Titanium Dioxide, Simethicone, Alumina | Eusolex ® T-2000 (Rona) | 5.00 |
| Phase B-1 | | |
| Demineralized water | | 66.10 |
| Chitosan, water | Hydagen ® CMF (Henkel) | 2.00 |
| Glycerin USP | Emery 916 (Henkel) | 2.50 |
| Dimethicone copolyol phosphate | Pecosil PS-100 (Phoenix Chemical) | 2.50 |
| Phase B-2 | | |
| Polyquaternium 37, Mineral oil, PPG-1 trideceth-6 | Salcare SC 95 (Ciba) | 0.40 |
| Phase C | | |
| Propylene Glycol, DMDM Hydantoin, | Paragon ™ II (McIntyre) | 0.70 |
| Methylparaben, Propylparaben | | |
| Total | | 100.00 |

Procedure

Combine A-1; stir and heat to 60° C until all solids are dissolved. Disperse A-2 in A-1 with agitation. Combine B-1; stir and heat to 60° C. Disperse B-2 in B-1 with agitation. Add A to B while stirring vigorously. Gently homogenize allowing mixture to cool to 40° C. Add C to A/B: gently homogenize until mixture is uniform. Stir with anchor mixer allowing mixture to reach 25° C. prior to packaging. Use a high shear pump spray device for dispensing (e.g., Eurogel pump by Seaquist Perfect)

| Formulation 3: Sunscreen Cream | | |
|---|---|---|
| INCI Name | Trade Name/Manufacturer | % w/w |
| Phase A | | |
| Deionized water | | 39.73 |
| Carbomer (2% aq. solution) | Carbopol 980/BF Goodrich | 15.00 |
| Propylene Glycol | | 5.00 |
| Methylparaben | | 0.20 |
| Propylparaben | | 0.10 |
| Triethanolamine (99%) | | 0.45 |
| Tetrasodium EDTA | | 0.02 |
| Phase B | | |
| Octyl Methoxycinnamate | Eusolex ® 2292/Rona | 5.00 |
| Benzophenone-3 | Eusolex ® 44360/Rona | 3.00 |
| Di-isoamyl-3,5-dimethoxy-4-hydroxybenzylidene malonate | | 4.50 |
| Glyceryl Stearate (and) PEG-100 Stearate | Ariacel 165/ICI Surfactants | 1.00 |
| Cyclomethicone | Dow Corning 344 Fluid/Dow Corning | 5.00 |
| Glyceryl Stearate | | 4.00 |
| Stearic Acid | Emersol 132, NF/Henkel | 2.50 |
| Isostearyl Isostearate | Prisonne ISIS 2039/Unichema | 10.00 |
| Hydrogenated Castor Oil | Castorwax/CasChem | 2.00 |
| $C_{12-15}$ Alcohols Benzoate | Finsolv TN/Finetex | 2.50 |
| Total | | 100.00 |

Procedure

Add Phase A ingredients to main vessel under impeller agitation. Heat phase A to 75–80° C. Combine Phase B ingredients; heat and nix to 85° C. Slowly add Phase B to batch; mix for 15 minutes at 85° C. Remove from heat; switch to paddle mixing and cool to room temperature.

Procedure

Combine A-1; stir and heat to 55–60° C. until all solids are dissolved. Disperse A-1 in A-1 by propeller agitation. Combine B; stir and heat to 50–55° C. Slowly add B to A while stirring vigorously. Add C to A/B; gently homogenize until mixture is uniform. Stir with anchor mixer allowing mixture to cool to room temperature.

Formulation 4: Water/Oil Broad Spectrum Sunscreen Lotion

| INCI Name | Trade Name/Manufacturer | % w/w |
|---|---|---|
| Phase A-1 | | |
| Octyl Methoxycinnamate | Eusolex ® 2292/Rona | 7.50 |
| Iso-amyl-alpha-acetyl-3,5-dimethoxy-4-hydroxy-cinnamate | | 5.00 |
| Octyl Stearate | Cetiol 868/Henkel | 2.00 |
| Dicapryl Ether | Cetiol OE/Henkel | 3.00 |
| Cyclomethicone | Dow Corning 345 Fluid/Dow Corning | 4.00 |
| Dimethicone | DC 200 fluid 50 cST/Dow Corning | 2.00 |
| PEG-30 Dipolyhydroxystearate | Ariacel P135/ICI | 1.30 |
| Laurylmethicone copolyol | Dow Corning formulation Aid 5200/Dow | 2.30 |
| Behenamidopropyl dimethylamine Behenate | Catemol 220-B/Phoenix Chemical | 0.50 |
| Phase A-2 | | |
| Titanium Dioxide (and) Alumina (and) Simethicone | Eusolex ® T-2000/Rona | 8.00 |
| Deionized Water | | 61.00qs |
| Propylene Glycol | | 2.00 |
| Sodium Chloride | | 0.80 |
| Phase C | | |
| DMDM Hydantoin, Methylparaben, Propylparaben | Paragon II/McIntyre | 0.60 |
| Total | | 100.00 |

Formulation 5: UVA/UVB Sun Protection Cream with Avobenzone

| INCI Name | Trade Name/Manufacturer | % w/w |
|---|---|---|
| Phase A-1 | | |
| Water (demineralized) | | 67.80 |
| Disodium EDTA | | 0.05 |
| Propylene glycol | | 3.00 |
| Methylparaben | | 0.15 |
| Phase A-2 | | |
| Carbomer | Carbopol Ultrez 10/BF Goodrich | 0.20 |
| Phase B | | |
| Isopropyl Myristate | | 2.00 |
| Cetyl Alcohol, Glyceryl Stearate, PEG-75 Stearate, Ceteth 20, Steareth 20 | Emulium Delta/Gattefosse | 4.00 |
| Diethyl-3,5-dimethoxy-4-hydroxybenzylidene malonate | | 3.50 |
| Homomethyl salicylate | Eusolex ® HMS/Rona | 7.00 |
| Octyl salicylate | Eusolex ® OS/Rona | 7.00 |
| Butyl methoxydibenzoylmethane | Eusolex ® 9020/Rona | 3.00 |
| Dimethicone | Dow Corning Fluid 200, 100 sct/Dow | 1.00 |
| C30–38 Olefin/Isopropyl Maleate/MA Copolymer | Performa V 1608/New Phase Technologies | 1.00 |
| Phase C | | |
| Triethanolamine (99%) | | 0.30 |
| Phase D | | |
| preservatives | | q.s. |
| Total | | 100.00 |

Procedure

Combine A-1; heat to 50° C. while stirring until methylparaben is dissolved.

Disperse A-2 in A-1 with a sifter. Heat A to 65° C.

Combine B; heat to 65–70° C. while stirring until solids are dissolved.

Add B to A. Homogenize

Add C at 55–60° C. Continue to homogenize allowing mixture to cool to 40–45° C.

Add D; stir with propeller mixer until uniform.

Adjust pH with TEA to 6.5–7.0

Procedure

Prepare Phase B by dispersing Carbopol in water. Heat the dispersion to 70–75° C.

Combine Phase A ingredients. Stir and heat to 70–75° C.

Add Phase B to Phase A while stirring.

Add Phase C. Homogenize until mixture cools to 45–40° C.

Add Phase D. Stir allowing mixture to cool to room temperature.

Formulation 6: Oil/Water Sunscreen Lotion

| INCI Name | Trade Name/Manufacturer | % w/w |
|---|---|---|
| Phase A | | |
| Diisoamyl-3,5-dimethoxy-4 hydroxybenzylidene malonate | | 3.00 |
| Isopropyl Myristate | Emerest 2314/Henkel | 4.00 |
| C12–15 Alkyl Benzoate | Finsolv TN/Finetex | 4.00 |
| Cetyl Alcohol | Crodacol C-70/Croda | 1.50 |
| Steareth-2 | Bnj 72/ICI Surfactants | 2.00 |
| Steareth-21 | Bnj 721/ICI Surfactants | 2.50 |
| Dimethicone | Dow Corning Fluid 200, 100 sct/Dow | 0.50 |
| Phase B | | |
| Deionized Water | | 81.07 |
| Acrylates/C10–30 Alkyl Acrylates Crosspolymer | Carbopol ETD 2020/BP Goodrich | 0.20 |
| Phase C | | |
| Triethanolamine (99%) | TEA 99%/Union Carbide | 0.23 |
| Phase D | | |
| Phenoxyethanol (and)isopropylparaben (and)isobutylparaben(and)butylparaben | Liquapar PE/Sutton | 1.00 |
| Total | | 100.00 |

Formulation 7: Oil/Water Sunscreen Lotion

| INCI Name | Trade Name/Manufacturer | % w/w |
|---|---|---|
| Phase A | | |
| Avobenzone | Eusolex 9020/Rona | 3.00 |
| Diisoamyl-3,5-dimethoxy-4-hydroxybenzylidene malonate | | 3.00 |
| Isopropyl Myristate | Emerest 2314/Henkel | 4.00 |
| C12–15 Alkyl Benzoate | Finsolv TN/Finetex | 4.00 |
| Cetyl Alcohol | Crodacol C-70/Croda | 1.50 |
| Steareth-2 | Bnj 72/ICI Surfactants | 2.00 |
| Steareth-21 | Bnj 721/ICI Surfactants | 2.50 |
| Dimethicone | Dow Corning Fluid 200, 100 sct/Dow | 0.50 |
| Phase B | | |
| Deionized Water | | 78.07 |
| Acrylayes/C10–30 Alkyl Acrylates Crosspolymer | Carbopol ETD 2020/BF Goodrich | 0.20 |
| Phase C | | |
| Triethanolamine (99%) | TEA 99%/Union Carbide | 0.23 |
| Phase D | | |
| Phenoxyethanol (and) isopropylparaben (and)isobutylparaben (and) butylparaben | Liquapar PE/Sutton | 1.00 |
| Total | | 100.00 |

Procedure

Preapare Phase B by dispersing Carbopol in water. Heat the dispersion to 70–75° C.

Combine Phase A ingredients. Stir and heat to 70–75° C.

Add Phase B to Phase A while stirring.

Add Phase C. Homogenize until mixture cools to 45–40° C.

Add Phase D. Stir allowing mixture to cool to room temperature.

It has been found that to provide antioxidant functionality, the phenyl group of the compounds of formula I should have a substituent pattern of "3,5-alkoxy, 4-hydroxy." Compounds of formula I also have a moiety, A, which provides UV absorbing functionality, (chromophoric in the UV range). Moiety A, can vary widely in structure with examples given in formulae II, III and IV above.

The compounds of Formula I–IV can be obtained by condensation of a corresponding 3,5-dialkoxy, 4-hydroxy benzaldehyde of formula B,

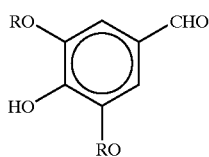

B wherein R is as defined above, with a compound that provides the U-V absorbing moiety, "A" as defined above. An example is a compound of the formula: $R_1-CH_2-C(O)XR_2$ wherein $R_1$ and $R_2$ and X are as defined above for formulae II–IV.

The benzaldehyde of formula B can be obtained commercially or prepared from 3,4, 5-trimethoxybenzaldehyde through selective monodemethylation at the 4-position. This technique leads to syringaldehyde. The syringaldehyde is then condensed with a compound to provide the desired UV absorbing moiety "A".

The entire disclosure of all applications, patents and publications, cited above are hereby incorporated by reference.

EXAMPLES

Example I

Ethyl-alpha-cyano-3,5-dimethoxy-4-hydroxy Cinnamate

Monodemethylation of 3,4,5-trimethoxy benzaldehyde using sulphuric acid at 40° C. for 8 hours yields 3,5-Dimethoxy-4-hydroxy benzaldehyde (Syringaldehyde). Condensation of syringaldehyde with ethyl cyanoacetate in the presence of piperidine—acetic acid and benzene as the reaction medium at reflux temperature under continuous azeotropic water removal yields the title product. The reaction takes about 1.5 hours for completion. The yield obtained is typically 95%.

Example II

Diethyl-3,5-dimethoxy-4-hydroxy Benzylidene Malonate

Monodemethylation of 3,4,5-trimethoxybenzaldehyde using sulphuric acid at 40° C. for 8 hours as described above in Example 1 yields syringaldehyde. Condensation of 3,5-Dimethoxy-4-hydroxy benzaldehyde (Syringaldehyde) with diethyl malonate in the presence of piperidine—acetic acid and benzene as the reaction medium at reflux temperature under continuous azeotropic water removal yields the title product. The reaction takes about 7.5 hours for completion.

Example III

Ethyl-alpha-methyl-3,5-dimethoxy-4-hydroxy Cinnamate

Monodemethylation of 3,4,5-trimethoxy benzaldehyde using sulphuric acid at 40° C. for 8 hours as described above in Example 1 yields syringaldehyde. The Wittig salt is prepared by reaction of triphenyl phosphine and ethyl-2-bromopropionate in benzene media at 70–75 ° C. for 8 hours and subsequent basification with 1N Sodium hydroxide to phenolphthalein end point at room temperature. Extraction with benzene, concentration of the benzene extract and the addition of petroleum ether (60–80° C.) yield triphenyl methyl carbethoxy methylene phosphorane as a solid product. Condensation of 3,5-Dimethoxy-4-hydroxy benzaldehyde (Syringaldehyde) with triphenyl methyl carbethoxy methylene phosphorane is performed at reflux temperature in xylene for seven hours and after work up, yields the title compound.

Example IV

Ethyl-alpha-acetyl-3,5-dimethoxy-4-hydroxy-cinnamate

Monodemethylation of 3,4,5-trimethoxy benzaldehyde using sulphuric acid at 40° C. for 8 hours as described above in Example 1 yields syringaldehyde. Condensation of 3,5-Dimethoxy-4-hydroxy benzaldehyde (syringaldehyde) with ethyl acetoacetate in the presence of piperidine—acetic acid and benzene as the reaction medium at reflux temperature yields the title product. The reaction takes about 3.5 hours for completion.

Example VI

Di-(2-Ethylhexyl)-3,5-dimethoxy-4-hydroxy Benzylidene Malonate

Monodemethylation of 3,4,5-trimethoxy benzaldehyde using sulphuric acid at 40° C. for 8 hours as described above in Example 1 yields syringaldehyde. Transesterfication of diethyl malonate using 2-ethylhexyl alcohol in neat condition at 140–155° C. for 2 hours under nitrogen blanketing in the presence of sulphuric acid and after work up, followed by high vacuum distillation, yields di-6-ethylhexyl malonate. Condensation of 3,5-Dimethoxy-4-hydroxy benzaldehyde (Syringaldehyde) with di-2-ethylhexyl malonate in the presence of piperidine—acetic acid and benzene as the reaction medium at reflux temperature under continuous azeotropic water removal yields di-2-ethylhexyl-3,5-dimethoxy-4-hydroxy benzylidene malonate. The reaction takes about nine hours for completion. The yield typically obtained is 91%.

Example VII

Di-isoamyl-3,5-dimethoxy-4-hydroxy Benzylidene Malonate

Example VI was repeated, except in the condensation step, di-2-ethyhexyl malonate was replaced with di-isoamyl malonate. The yield typically obtained was over 90%.

Example VIII

Di-isopropyl-3,5-dimethoxy-4-hydroxy Benzylidene Malonate

Example VI was repeated, except in the condensation step, di-2-ethyhexyl malonate was replaced with di-isopropyl malonate. The yield typically obtained was over 90%.

Example IX

Di-dodecyl-3,5-dimethoxy-4-hydroxy Benzylidene Malonate

Example VI was repeated, except in the condensation step, di-2-ethyhexyl malonate was replaced with di-dodecyl malonate. The yield typically obtained was over 90%.

Example X

Iso-propyl-alpha-acetyl-3,5-diimethoxy-4-hydroxy-cinnamate

Example IV was repeated, except in the condensation step, ethyl acetoacetate was replaced with iso-propyl acetoacetate. The yield of the desired product was 88%.

Example XI

Iso-butyl-alpha-acetyl-3,5-dimethoxy-4-hydroxy-cinnamate

Example IV was repeated, except in the condensation step, ethylacetoacetate was replaced with iso-butyl-acetoacetate. The yield of the desired product was 89%.

Example XII

Iso-amyl-alpha-acetyl-3,5-dimethoxy-4-hydroxy-cinnamate

Example IV was repeated, except in the condensation step, ethylacetoacetate was replaced with iso-amyl acetoacetate. The yield of the desired product was 89%.

Comparative Example A

Ethyl-alpha-cyano-3,4,5-trimethoxy Cinnamate

Condensation of 3,4,5-trimethoxy benzaldehyde with ethyl cyanoacetate in the presence of piperidine—acetic acid and benzene as the reaction medium at reflux temperature under continuous azeotropic water removal yields the title product. The reaction takes about three hours for completion and the yield obtained is typically 90%.

Comparative Example B

Diethyl-3,4,5-trimethoxy Benzylidene Malonate

Condensation of 3,4,5-trimethoxy benzaldehyde with diethyl malonate in the presence of piperidine—acetic acid and benzene as the reaction medium at reflux temperature under continuous azeotropic water removal yields the title product. The reaction takes about ten hours for completion. The yield obtained is typically 85%.

COMPARATIVE TESTS

Figure 1:
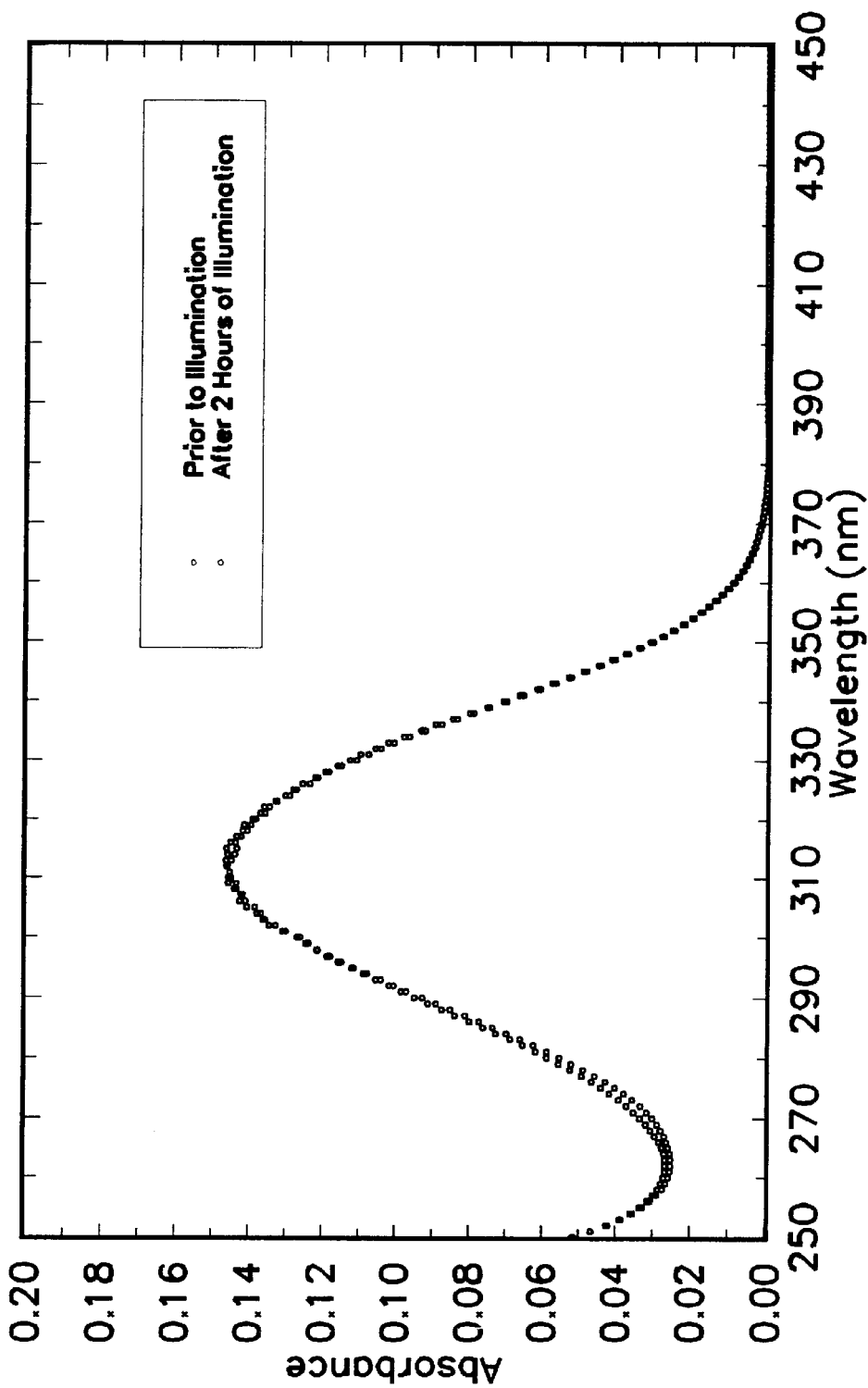
FIGS. 1–5 are graphs of absorbance prior to and after illumination to show photostability of the compound.
Figure 2:
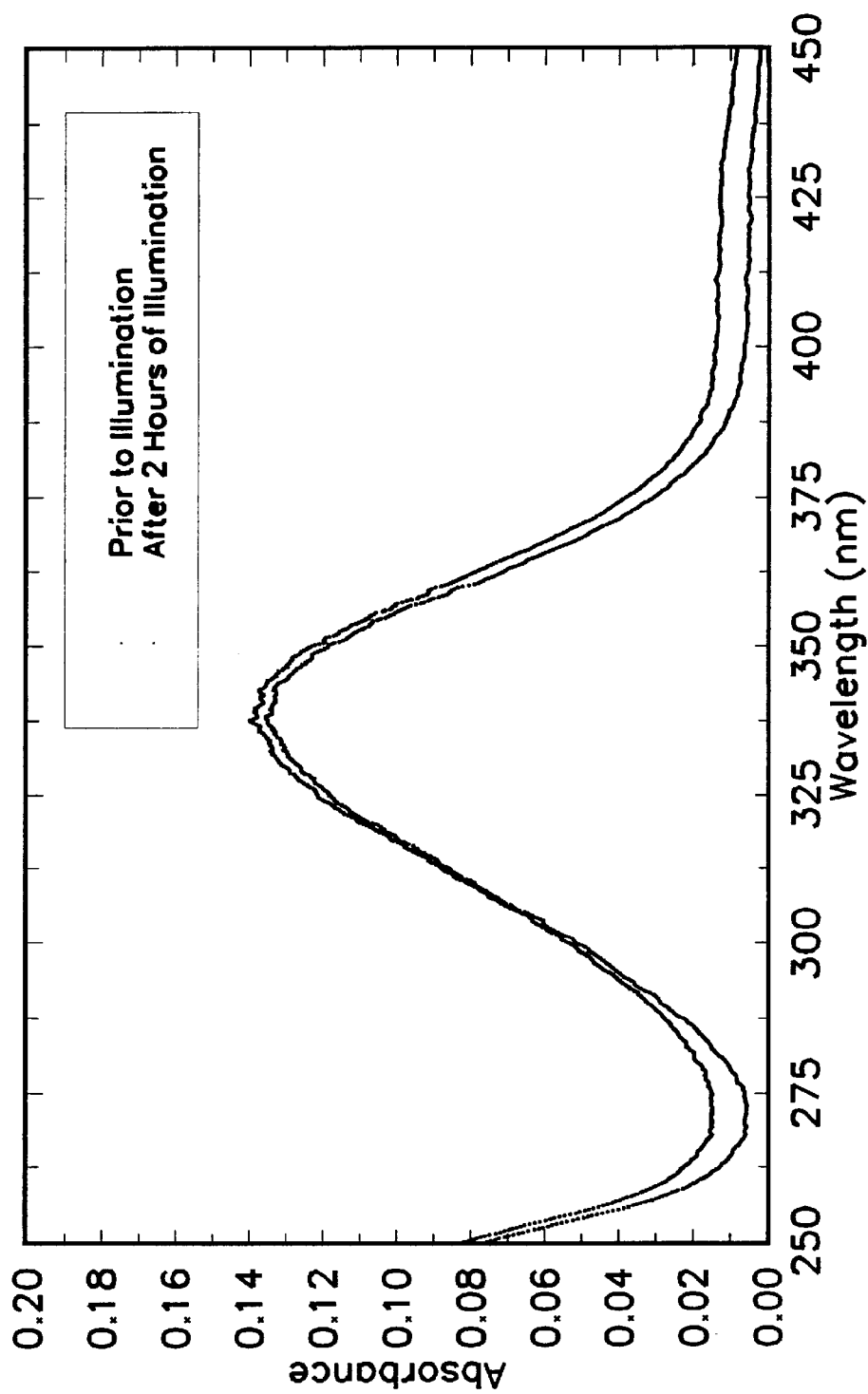
Figure 3:
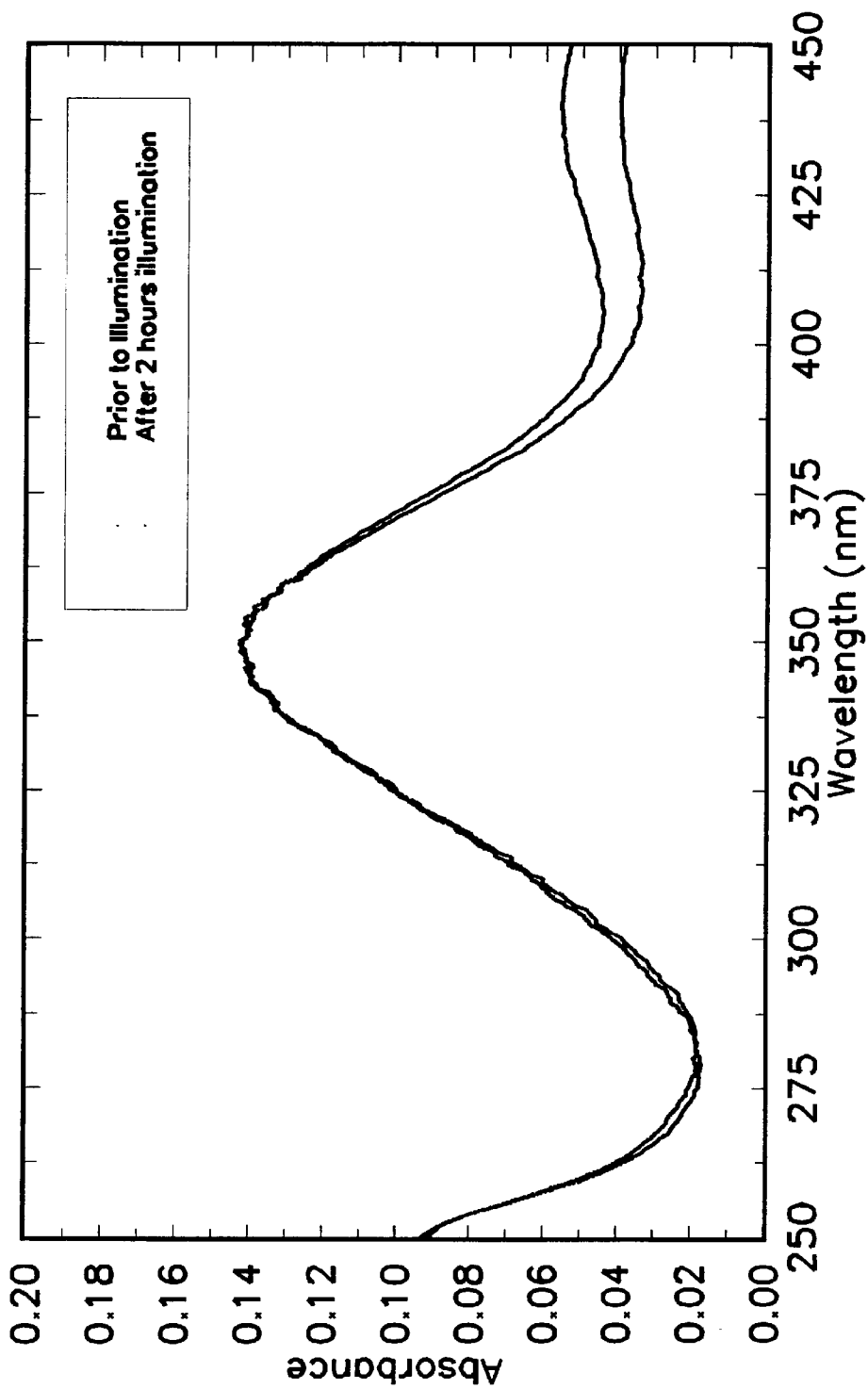
Figure 4:
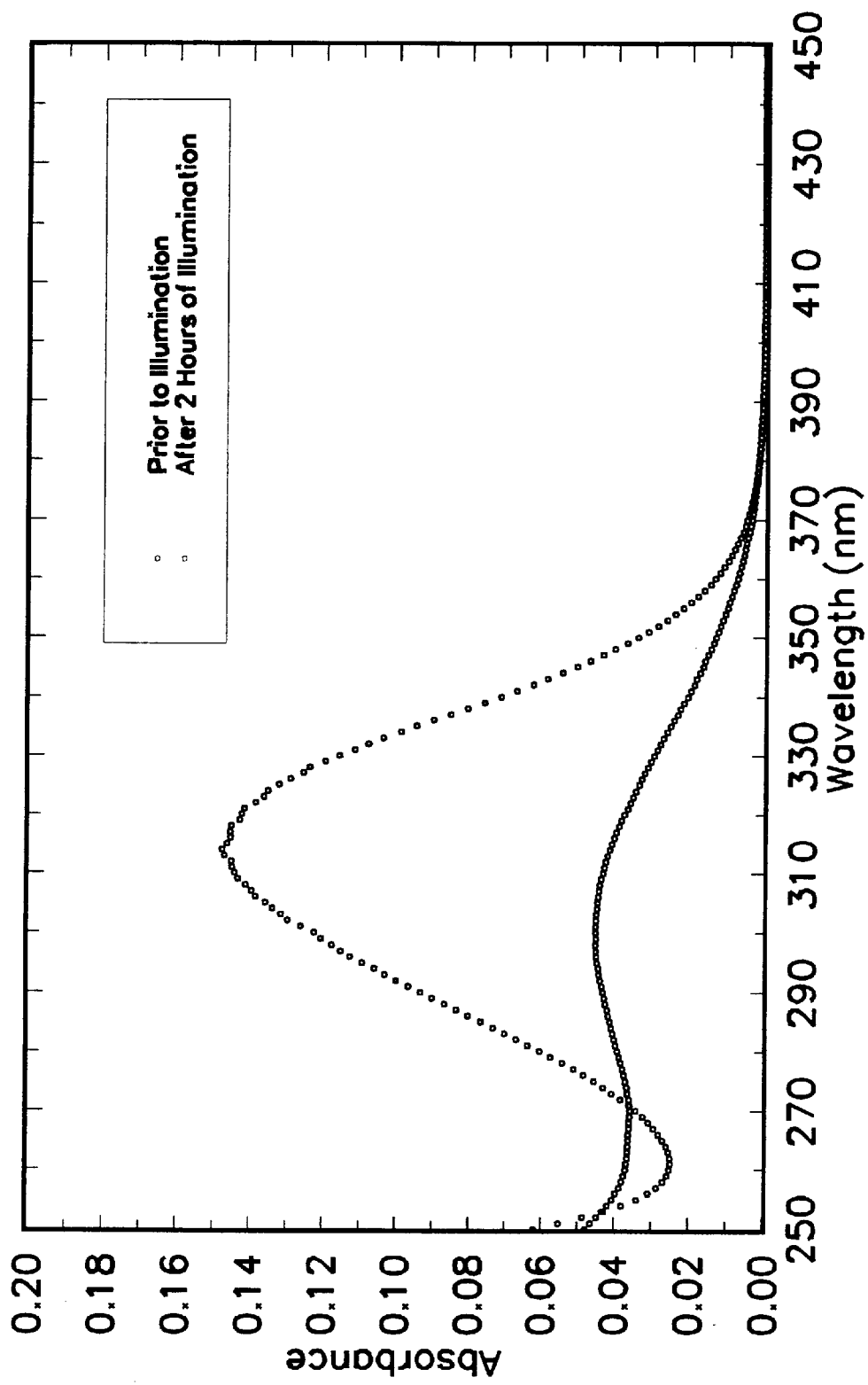
Figure 5:
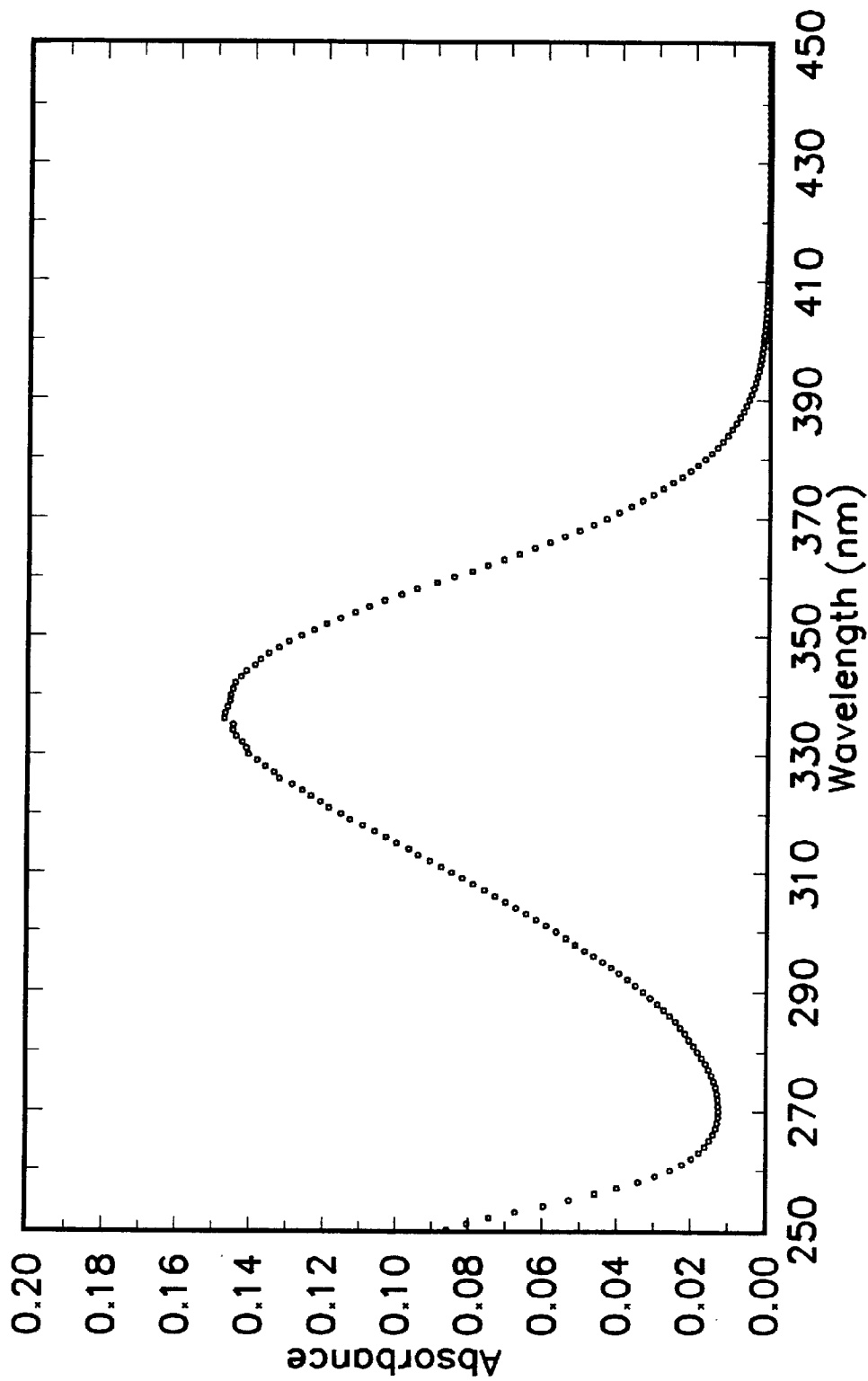

Sunscreen compounds selected from the list below were evaluated for antioxidant activity, photostability and their ability to stabilize Avobenzone.

2/1 diethyl-3,4,5-trimethoxy benzylidene malonate
2/2 ethyl-alpha-cyano-3,4,5-trimethoxy cinnamate
2/3 ethyl-alpha-cyano-3,5-dimethoxy-4-hydroxy cinnamate
2/4 diethyl-3,5-dimethoxy-4-hydroxy benzylidene malonate
2/5 ethyl-alpha-acetyl-3,5-dimethoxy-4-hydroxy cinnamate
2/7 ethyl-alpha-methyl-3,5-dimethoxy-4-hydroxy cinnamate
2/8 di(2-ethyl-hexyl)-3,5-dimethoxy-4-hydroxy benzylidene malonate
2/10 di-iso-amyl-3,5-dimethoxy-4-hydroxy benzylidene malonate DPPH Test Method A DPPH concentrate (2.5×) of 25 mg of 1,1-Diphenyl-2-Picyrl-Hydrazyl ACS# 1898-66–4 (Sigma #D-9132, lot 99H3601) dissolved in 250 mL ethanol (USP), is prepared fresh on the measurement date. A DPPH working solution is then prepared by diluting 100 mL of this concentrate to a final volume of 250 mL (100 $\mu$M/mL). A blank 13×100 mm borosilicate glass screw top tube of ethanol (USP) is used to zero the spectrometer (Milton Roy, Spectronic 20+) at 517 nm and a control tube of DPPH working solution is measured under identical conditions, and taken as 0% activity. Aliquots of the 0.25% & 0.5% (RT & 45° C.) test solution are added to tubes followed by the rapid addition of 4 mL DPPH working solution then rapidly capped and mixed. After 20 minutes, the absorbance of each sample is read at 517 nm.

The percent reducing activity (% RA) is calculated using the following equation:

$$\% \text{ Reduction Activity} = 100 \, A(0)\text{-}A(20)/A(0)$$

Where A(0) is the absorbance value of the DPPH working solution at 517 nm zeroed against an ethanol blank and A(20) is the absorbance at 517 nm, 20 minutes after combining the antioxidant with the DPPH working solution.

The concentration of antioxidant (mg/ml) in the final assay mixture is calculated based on the dilution of respective aliquots of each compound in the final assay volume and % RA tabulated and plotted as percent activity at each concentration in the dilution series.

Antioxidant Property

Table 2 shows the antioxidant property of selected compounds (2/1, 2/2, 2/3, 2/4, 2/5, 2/7, 2/8 and 2/10) in % reducing activity.

TABLE 2

| | % Reducing Activity | | | | | | | |
|---|---|---|---|---|---|---|---|---|
| mg/ml | 2/1 | 2/2 | 2/3 | 2/4 | 2/5 | 2/7 | 2/8 | 2/10 |
| 2.500 | 0.0 | 3 | 25.40 | 71.70 | | | | |
| 0.278 | | | 15.5 | 33.4 | 59.9 | 85.0 | 33.7 | 30.1 |
| 0.139 | | | 11.3 | 29.51 | 47.3 | 77.3 | 23.2 | 22.3 |
| 0.056 | | | 8.4 | 12.8 | 31.0 | 61.2 | 13.0 | 14.6 |
| 0.028 | | | 5.2 | 5.2 | 20.7 | 46.1 | 8.5 | 10.2 |

Compounds with 3,5-dimethoxy-4-hydroxy substitution were found to exhibit much higher reducing activity (antioxidant activity) than compounds with 3,4,5-trimethoxy substitution. In order to boost antioxidant activity of the compounds of the present invention, other antioxidants can be combined. Some examples are those antioxidants mentioned above and Tocopherols, tocopherylacetate, Ascorbic acid, Emblica antioxidants, Proanthocyanidins (from pine bark, grape seed extract, and the like) green tea polyphenols, rosemary antioxidants, gallic acid, ellagic acid, butylhydroxy toluene (BHT), butylhydroxy anisole (BHA) and the like.

Photostability The photostability of selected compounds (2/1, 2/4, 2/5, 2/7 and 2/8) was tested according to the procedures below.

The solar simulator used for illumination of the samples in the experiments was constructed incorporating a 1 kw Xe arc lamp, optical bench and sample illumination chamber. The lamp output was filtered through a water filter with a course window to remove most of the infrared radiation and optical filters to remove wavelengths below 290 nm. The output of the illumination system was focused onto the face of a 1 cm quartz Cuvette that was thermally equilibrated with a constant temperature water bath at 25 ° C. A magnetic stir was mounted under the Cuvette so that the samples could be stirred while being illuminated. An electric shutter was controlled by a dark room timer to provide precise control of illumination times. The solar simulator was constructed to provide illumination that closely matches terrestrial sunlight. The solar simulator delivered roughly 250 J/cm$^2$ over a 2-hour period of illumination in a 290–490 nm range. This irradiance was determined using two nitrobenzaldehyde chemical actinometry. The irradiance is much higher than other solar simulator systems which typically illuminate a large area in order to illuminate many samples simultaneously rather than being focused down to a very small area.

Each exploratory sunscreen compound was dissolved in 70% ethanol/30% isopropyl myristate and/or 70% ethanol/30% water and the UV visible absorption spectrum measured with a Shimadza UV 2101-double beam spectrophotometer using the solvent as reference. A similar solution of Octocrylene was prepared and the UV-visible absorption spectrum measured. Each solution was then illuminated for two hours in the solar simulator. After illumination, the absorption spectrum was again measured each solution. The results are shown in FIGS. 1–5, respectively.

All tested compounds were found to be photostable after two hours of illumination in a Xe-arc solar simulator with the exception of two compounds 2/7 and 2/8. An examination of the UV-visible spectra (FIGS. 1–5) reveals that the 2/1, 2/4 and 2/5 sunscreen compounds retain most of their absorptivity after 2 hours of illumination in the solar simulator while 2/7 degraded significantly (72% loss of absorbance) during this illumination period. The absorption spectra for 2/8 after illumination was not precise but was found to be approximately 82% after the initial value over a 2 hour period of illumination. The Octocrylene solution was found to exhibit no loss in absorptivity after 2 hours of illumination in the solar simulator. Thus 2/1, 2/4 and 2/5 have comparable photo stabilities to Octocrylene under the experimental conditions employed.

The sunscreens 2/4 and 2/5 exhibit broad absorption bands that extend across the UV region in 70% ethanol and 30% isopropyl myristate. They exhibit lower molar absorption than Avobenzone but appear to be more stable than Avobenzone.

Stabilizing Activity

The stabilizing activity of selected compounds (2/1, 2/4, 2/5, 2/7 and 2/8) toward Avobenzone was tested and compared with a conventional product according to the procedures below.

Individual solutions of selected sunscreen compounds (2/1, 2/4, 2/5, 2/7 and 2/8) with Avobenzone were as follows. Each sunscreen compound was dissolved in 70% ethanol/30% $H_2O$ solution containing roughly an equal molar amount of Avobenzone. A similar solution containing Di-2-ethylhexyl-2,6-napthalene dicarboxylic acid (DENDA) and Avobenzone was also prepared. Each solution was then illuminated in the solar simulator as configured above for the photostability tests and aliquots of each solution were removed at 30-minute time intervals. These aliquots were injected into an HPLC and the loss of Avobenzone was followed with illumination time. The high performance liquid chromatograph (HPLC) used for all experiments reported therein incorporated a Spectra-Physics model P-200 pump with an Applied Biosystems model 785A UV-Visible detector with a Rheodyne manual injector incorporating a 50 ml sample loop and a 150×4.6 mm reversed-phase $C_{18}$ column (Alltech). All analyses were carried out under isocratic elution conditions using $CH_3OH/H_2O$ mixtures for the mobile phase at a flow rate of 1 $H_2O$ ml per minute. It was necessary to employ HPLC separation of Avobenzone from each of the sunscreen compounds to quantify Avobenzone due to the absorption spectra overlap with some of these compounds. General data regarding the absorbance characteristics of the sunscreen compounds and Avobenzone are presented in Table 3.

TABLE 3

Absorbance and Molar absorptivity data for sunscreen compounds measured in 70% ethanol/30% $H_2O$ solution

| Compound | λMax | $\epsilon\lambda Max(M^{-1}cm^{-1})$ |
|---|---|---|
| Avobenzone | 360 nm | $2.5 \times 10^4$ |
| 2/1 | 313 nm | $2.0 \times 10^4$ |
| 2/4 | 338 nm | $1.2 \times 10^4$ |
| 2/5 | 348 nm | $1.9 \times 10^4$ |
| 2/7 | 314 nm | N/A |
| 2/8 | 340 nm | $1.6 \times 10^4$ |

Figure 6:
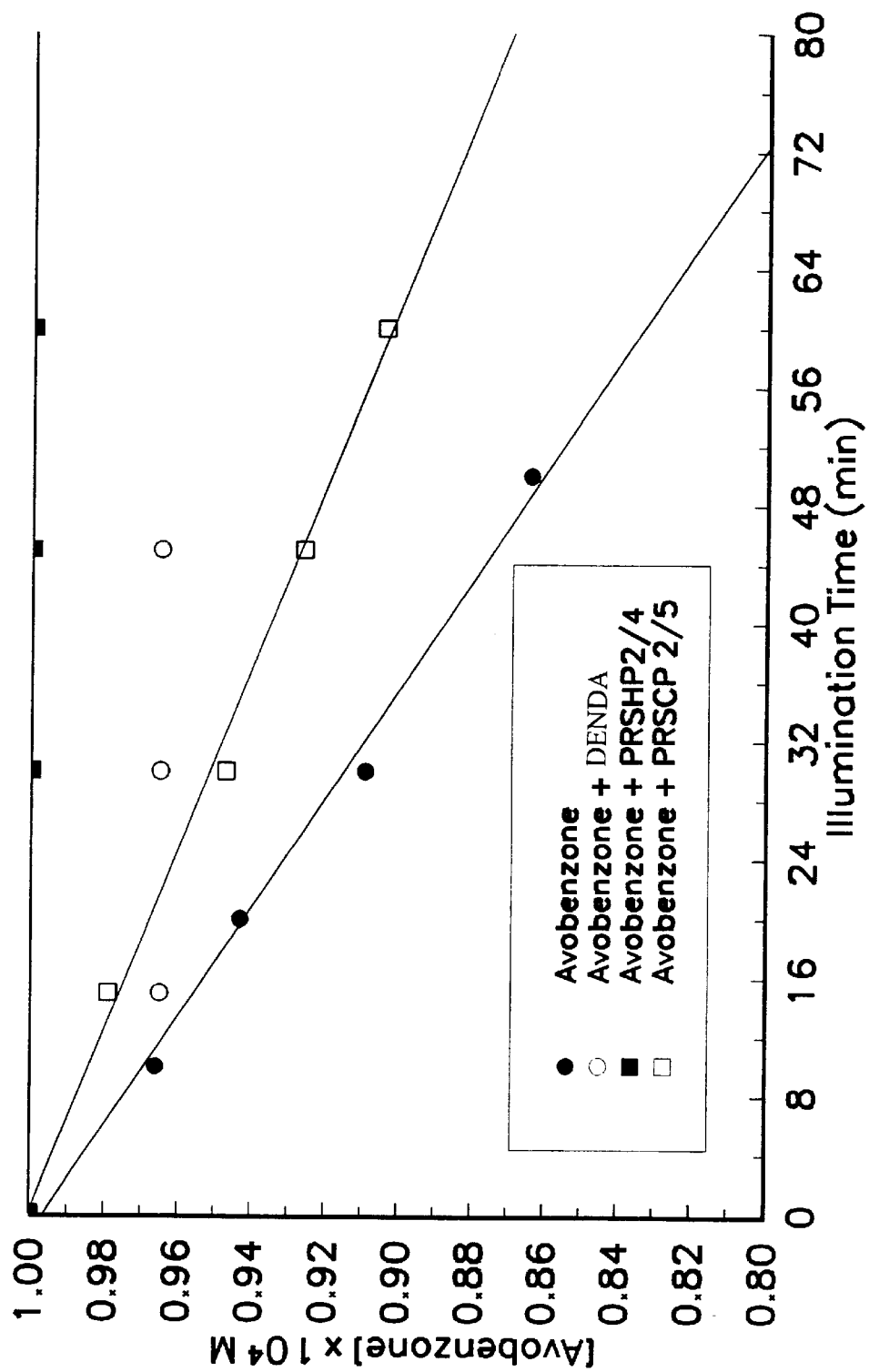
FIGS. 6 and 7 compare photostability of compounds to Avobenzone over time.
Figure 7:
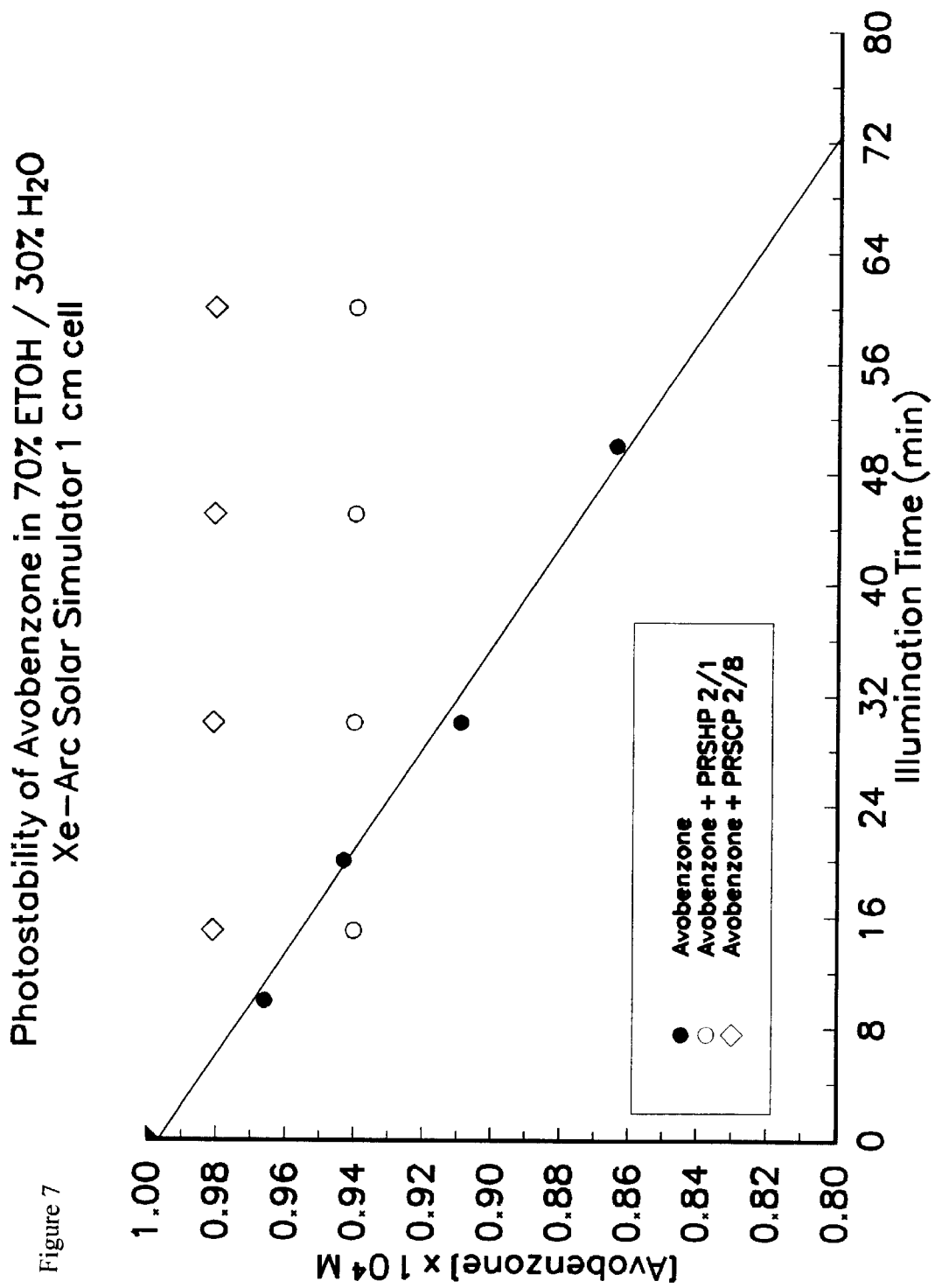

The loss of Avobenzone when illuminated alone in solution was rapid exhibiting a half life of approximately 3 hours in the solar simulator. FIGS. 6 and 7 reveal that the sunscreen compounds 2/4, 2/1 and 2/8 appear to stabilize Avobenzone as effectively as DENDA antioxidant. Compound 2/5 was somewhat less effective than DENDA. The loss of Avobenzone in the presence of DENDA was found to follow unusual kinetics. Initially the loss of Avobenzone was quite rapid but then seemed to become stable.

The preceding examples can be repeated with similar success by substituting the generically or specifically described reactants and/or operating conditions of this invention for those used in the examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula II

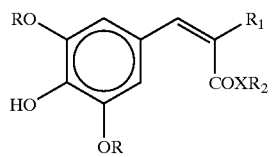

wherein
each R is independently linear or branched $C_1$ to $C_8$ alkyl;
$R_1$ is selected from the group consisting —$C(O)CH_3$, —$CO_2R_3$, —$C(O)NH_2$ and —$C(O)N(R_4)_2$;
X is O or NH;
$R_2$ is linear or branched $C_1$ to $C_{20}$ alkyl;
$R_3$ is linear or branched $C_1$ to $C_{20}$ alkyl; and
each $R_4$ is independently hydrogen or linear or branched $C_1$ to $C_8$ alkyl.

2. A compound of claim 1 wherein R is $C_1$–$C_4$ alkyl, X is oxygen and $R_2$ is linear or branched $C_1$ to $C_4$ alkyl.

3. A compound of claim 2 wherein $R_1$ is $CO_2R_3$ and, $R_3$ is linear or branched $C_1$ to $C_4$ alkyl.

4. A compound of claim 2 wherein $R_1$ is $C(O)CH_3$.

5. A compound of claim 2 wherein $R_1$ is —$C(O)N(R_4)_2$, and at least one $R_4$ is hydrogen and the other is hydrogen or linear or branched $C_1$ to $C_4$ alkyl.

6. A compound of claim 2 wherein $R_1$ is —$C(O)N(R_4)_2$, and each $R_4$ is independently linear or branched $C_1$ to $C_4$ alkyl.

7. A compound of claim 1 wherein R is $C_1$–$C_4$ alkyl, $R_1$ is —$CO_2R_3$, and at least one of $R_2$ and $R_3$ is linear or branched $C_8$ to $C_{20}$ alkyl.

8. A compound of claim 7 wherein $R_2$ and $R_3$ are each linear or branched $C_8$ alkyl.

9. A compound of claim 7 wherein at least one of $R_2$ and $R_3$ is linear or branched $C_{12}$ to $C_{20}$ alkyl.

10. A compound as in claim 1 wherein R is methyl or ethyl.

11. A compound of one of the formulae

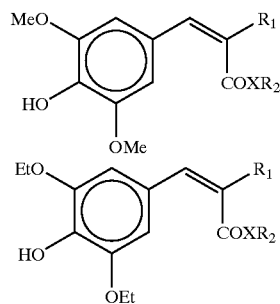

wherein
$R_1$ is selected from the group consisting —$C(O)CH_3$, —$CO_2$ ($C_1$–$C_8$ alkyl),
—$C(O)NH_2$, —$C(O)NH(C_1$–$C_4$ alkyl), and —$C(O)N$ ($C_1$–$C_4$ alkyl)$_2$;
X is O or NH; and
$R_2$ is $C_1$–$C_{12}$ alkyl.

12. A compound of claim 11 wherein X is oxygen and $R_2$ is linear or branched $C_1$ to $C_4$ alkyl and $R_1$ is selected from the group consisting of —$CO_2(C_1$–$C_4$ alkyl); —$C(O)NH$ ($C_1$–$C_4$ alkyl), —$C(O)CH_3$, —$C(O)NH_2$, and —$C(O)N$ ($C_1$–$C_4$ alkyl)$_2$.

13. A compound of claim 11 wherein $R_1$ is —$CO_2C_8H_{18}$.

14. A compound of claim 1 selected from the group consisting of ethyl- alpha- acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, dipalmitoyl-3,5-dimethoxy-4-hydroxy benzylidene malonate, di-dodecyl-3,5-dimethoxy-4-hydroxy benzylidene malonate, and di-isopropyl-3,5-dimethoxy-4-hydroxy benzylidene malonate.

15. A sunscreen formulation comprising a compound of claim 1 in an amount effective to adsorb illumination in a range above 320 nm wavelength.

16. A sunscreen formulation comprising a compound of claim 1 in an amount effective to absorb illumination in a range of 290 to 400 nm wavelength.

17. A sunscreen formulation as in claim 15, which comprises from 0.1 to 40 wt. % of a compound of formula II.

18. A sunscreen formulation as in claim 15 comprising an additional organic sunscreen agent for filtering UV-B, UV-A rays or both.

19. A sunscreen formulation as in claim 17 wherein the compound of Formula II stabilizes the additional sunscreen agent against degradation from exposure to light.

20. A sunscreen formulation as in claim 17, which additionally comprises an inorganic metal oxide sunscreen agent.

21. A personal care formulation that comprises a compound of formula II of claim 1 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

22. A personal care formulation as in claim 21 which is in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols.

23. A sunscreen formulation as in claim 18, which is free of photostabilizers other than compounds of formula II, which is present in an amount within the range of 0.1% to 40 wt % of said sunscreen formulation.

24. A method of protecting a substrate from UV radiation which comprises applying a sunscreen formulation of claim 15 to said substrate.

25. A method as of protecting a substrate of skin or hair from UV radiation which comprises applying a personal care formulation of claim 21 to a substrate of skin or hair.

26. A method of improving the photostability of a sunscreen formulation said method comprising adding a compound of formula II of claim 1 to said sunscreen formulation in an amount sufficient to improve the photostability of said sunscreen agent.

27. A method as in claim 26 wherein the amount of compound of formula II added to the sunscreen formulation falls within the range of 0.1% to 40 wt % of said sunscreen formulation.

28. A method as in claim 25 wherein the personal care formulation additionally comprises an antioxidant selected from the group consisting of tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

29. A personal care formulation comprising at least one compound of claim 1 and an antioxidant other than a compound of formula II.

30. A personal care formulation as in claim 29 wherein the antioxidant is selected from the group consisting of Tocopherols, tocopherylacetate, Ascorbic acid, Emblica antioxidants, Proanthocyanidins, Rosemary antioxidants, green tea polyphenols, gallic acid, ellagic acid, butylhydroxy toluene (BHT) and butylhydroxy anisole (BHA).

31. A personal care formulation which comprises a compound of formula II of claim 1 in an amount effective to protect formulation ingredients from oxidation.

32. A personal care formulation as in claim 31, which is in the form of lipsticks, foundation, make-up, loose or press powder, eye blush, eye shadows or nail lacquer.

33. A personal care formulation in a form selected from the group consisting of creams, ointment, suspensions, powders, oily lotions, oleo-alcoholic lotions, fatty gels, oleo-alcoholic gels, solid sticks, foams, emulsions, liquid dispersions, sprays and aerosols, wherein said personal care formulation comprises a compound of claim 1 in an amount effective to absorb illumination in a range above 320 nm wavelength, a cosmetically acceptable carrier and at least one cosmetic adjuvant selected from the group consisting of preservatives, antifoams, perfumes, oils, waxes, propellants, dyes, pigments, waterproofing agents, emulsifiers, surfactants, thickeners, humectants, exfoliants and emollients.

34. A method of improving the photostability of a sunscreen formulation said method comprising adding a compound of claim 1 to said sunscreen formulation in an amount sufficient to improve the photostability of said sunscreen formulation.

* * * * *